United States Patent [19]

O'Murchu

[11] Patent Number: 4,831,139
[45] Date of Patent: May 16, 1989

[54] PROCESS FOR THE PREPARATION OF 2-SUBSTITUTED 5-NITROSO-4,6-DIAMINOPYRIMIDINES

[75] Inventor: Colm O'Murchu, Visp, Switzerland

[73] Assignee: Lonza Ltd., Gampel/Valais, Switzerland

[21] Appl. No.: 244,591

[22] Filed: Sep. 13, 1988

Related U.S. Application Data

[63] Continuation of Ser. No. 847,246, Apr. 2, 1986, abandoned, which is a continuation-in-part of Ser. No. 566,887, Dec. 29, 1983, abandoned.

[30] Foreign Application Priority Data

Jan. 28, 1983 [CH] Switzerland ............................ 482/83
Dec. 6, 1985 [CH] Switzerland .......................... 5215/85

[51] Int. Cl.$^4$ ............................................ C07D 239/30
[52] U.S. Cl. .................................... 544/323; 544/317; 544/326
[58] Field of Search ........................ 544/323, 317, 326

[56] References Cited

U.S. PATENT DOCUMENTS 4,145,548 3/1979 Rose ..................................... 564/323

FOREIGN PATENT DOCUMENTS 1364734 5/1964 France ................................. 544/323
630616 6/1982 Switzerland ........................ 544/323

OTHER PUBLICATIONS

Barton ánd Ollis, Comprehensive Org. Chem. pp. 41–42, (1979).
Roberts and Caserio, Basic Principles of Organic Chemistry.
W. Traube, Ber., 37, 4544 (1904).
H. Sato et al., Chemical Abstracts, 47, 5946 (1953).
M. F. Mallette u.a., J. Am. Chem. Soc., 69, 1814 (1947).
E. C. Taylor u.a., J. Am. Chem. Soc., 81, 2442 (1959).

*Primary Examiner*—Mary C. Lee
*Assistant Examiner*—J. Richter
*Attorney, Agent, or Firm*—Fisher, Christen & Sabol

[57] ABSTRACT

Process for the preparation of 2-substituted 5-nitroso-4,6-diaminopyrimidines. Malonic dinitrile and amidine are nitrosated in the presence of a nitrite salt, to form the corresponding amidine salt of isonitrosomalononitrile. The latter is converted to the end product in the presence of an aprotic polar solvent by heat treatment in a basic medium.

11 Claims, No Drawings

PROCESS FOR THE PREPARATION OF 2-SUBSTITUTED 5-NITROSO-4,6-DIAMINOPYRIMIDINES

This application is a continuation of application Ser. No. 847,246, filed Apr. 2, 1986, now abandoned, which is a continuation-in-part of Ser. No. 566,887 filed Dec. 29, 1983, now abandoned.

BACKGROUND OF THE INVENTION

1. Field of the Invention

The invention relates to a process for the preparation of 2-substituted 5-nitroso-2,6-diaminopyrimidines.

2. Prior Art

It is known that 5-nitroso-2,4,6-triaminopyrimidine can be prepared from malonic dinitrile and a guanidine salt.

2,4,6-Triaminopyrimidine is obtained in moderate yield by the condensation of malonic dinitrile and guanidine hydrochloride or nitrate in the presence of a sodium alcoholate in alcoholic solution [W. Traube, Ber. 37, 4544 (1904); H. Sato et al., J. Chem. Soc. Japan Pure Chem. Sect. 72, 866 (1951); and Chem. Abstr. 47, 5946 (1953)]. This pyrimidine is then nitrosated to 5-nitroso-2,4,6-triaminopyrimidine, using nitrous acid [M. F. Mallette et al., J. Am. Chem. Soc. 69, 1814 (1947)]. such processes have the disadvantages that they are too troublesome when relatively large amounts have to be prepared and that the maximum yield of 5-nitroso-2,4,6-triaminopyrimidine is 75 to 78 percent, relative to malonic dinitrile.

Attempts have been made to simplify the process by not isolating the intermediate product 2,4,6-triaminopyrimidine (see Swiss Patent Specification No. 630,616 or U.S. Pat. No. 4,145,548). However, the process still has various disadvantages: expensive sodium alchololate has to be used; at least two mols of salt (NaCl and Na acetate) are precipitated per mol of malonic dinitrile employed; the reaction has to be carried out using relatively dilute solutions (approximately 2 liters of solvent per mol of product); and finally, the recovery of the solvent is a very difficult procedure, since a 4-component solvent mixture (methanol, ethanol, glacial acetic acid, water and by-products) is present.

Another route for the preparation of 5-nitroso-2,4,6-triaminopyrimidine is described by E. C. Taylor, O. Vogl and C. C. Cheng in J. Am. Chem. Soc. 81, 2442 (1959). 5-Nitroso-2,4,6-triaminopyrimidine is obtained in 88 percent yield by heating the potassium salt of isonitroso-malononitrile with guanidine carbonate in dimethylformamide. Since the potassium salt is prepared from the silver salt of isonitrosomalononitrile, the process is unsuitable for large-scale industrial production.

French Patent Specificaion No. 1,364,734 describes a process in which first malonic dinitrile in aqueous acetic acid solution is nitrosated with sodium nitrite, and then the resultant isonitrosomalononitrile solution is treated with guanidine carbonate, $CO_2$ being evolved and the guanidine salt of isonitrosomalononitrile being obtained by precipitation. The salt suspension is then cooled to approximately 0° C. and filtered, and the guanidine salt of isonitrosomalononitrile is dried. After the addition of $K_2CO_3$ to the salt in dimethylformamide, the mixture is heated under reflux in order to effect isomerization to 5-nitroso-2,4,6-triaminopyrimidine.

Such process represents a certain degree of progress compared with the process according to Taylor et al., but it still has several disadvantages. Thus, the acetic acid has to be used in excess (10 percent, according to the example). This excess has to be neutralized with guanidine carbonate in order for the formation of the guandine salt of isonitrosomalononitrile to go to completion.

Cooling the aqueous suspension to approximately 0° C. involves technical difficulties, since a crust of ice is formed on the inside of the reaction vessel. When the mixture is cooled to temperatures which are not quite so low, the salt is not completely precipitated.

From the point of view of safety, drying the guanidine salt of isonitrosomalononitrile involves risks.

In the treatment of crude isonitrosomalononitrile solution with guandine carbonate, one equivalent of $CO_2$ is liberated. The reaction mixture therefore has a tendency to foam during the operation and accordingly the reaction vessel cannot be optimally utilized.

BROAD DESCRIPTION OF THE INVENTION

An object of the invention is to avoid the above-mentioned disadvantages. Another object of the invention is to provide a process which makes it possible to prepare 2-substituted 5-nitroso-4,6-diaminopyrimidines in a simple and economical manner and in high yield. Other objects and advantages of the invention are set out herein or are obvious herefrom to one ordinarily skilled in the art.

The objects and advantages of the invention are achieved by the processes and compositions of the invention.

One embodiment of the invention involves a process for the preparation of 2-substituted 5-nitroso-4,6-diaminopyrimidines of the formula:

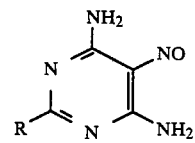

wherein R is aryl, alkyl, alkylthio, amino, substituted amino or arylalkyl. Malonic dinitrile is reacted with an amidine of the formula:

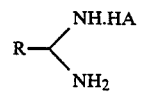

wherein A is Cl, $\frac{1}{2}SO_4$, $HSO_4$, $NO_3$, acetate or phosphate and R has the above meaning, in water or alcohol, in an acidic medium, and in the presence of a nitrite salt, to provide the corresponding amidine salt of isonitrosomalononitrile. The amidine salt of the isonitrosomalononitrile, in dimethylformamide or a pyridine base, and in a basic medium, is converted by heat treatment to the corresponding 2-substituted 5-nitroso-4,6-diaminopyrimidine.

In the first process of the invention, the malonic dinitrile, in water or alcohol as the solvent, is nitrosated with an amidine in an acidic medium and in the presence of a nitrite salt. The amidine salt of isonitrosomalononitrile is directly formed in the aqueous or alcoholic suspension. Such salt is not isolated; instead, the mixture is rendered basic. Then, after dimethylformamide or a pyridine base has been added, the water or the alcohol is distilled off under reduced pressure. After the water or the alcohol has been virtually completely removed, the reaction mixture is subjected to heat treatment, advantageously heated under reflux. The corresponding 2-substituted 5-nitroso-4,6-diaminopyrimidine is formed. As used herein acidic medium or acidic pH means a pH value of below 6.9. Also as used herein, basic medium or basic pH means a pH value of above 7.1.

The amount of solvent (water or ethanol) for the first stage of the reaction is not critical, and is advantageously 200 to 2,000 ml per mol of malonic dinitrile. Preferably 300 to 400 ml of solvent are employed per mol of malonic dinitrile.

In the second stage of the reaction, with dimethylformamide or a pyridine base as the solvent, 100 to 2,000 ml, preferably 300 to 500 ml, of solvent can be employed per mol of malonodinitrile.

In a preferred version of the first embodiment, 5-nitroso-2,4,6-triaminopyrimidine is prepared as follows: malonic dinitrile and guanidine hydrochloride are reacted as a pH of below 6.9 in the presence of sodium nitrite to give the guanidine salt of isonitrosomalononitrile, and the guanidine salt of isonitrosomalononitrile is converted to 5-nitroso-2,4,6-triaminopyrimidine by boiling under reflux in dimethylformamide.

After the isomerization reaction, the red suspension of 5-nitroso-2,4,6-triaminopyrimidine in dimethylformamide can be diluted with water, and the product can be separated off by filtration or centrifuging, and washed with water. For many reactions, the moist product can be used. If necessary, it can be dried by heating by any convenient method. 5-nitroso-2,4,6-triaminopyrimidine is a versatile intermediate product for example for the preparation of medicaments, such as, triamterene and methotrexate, and for the preparation of dyestuff components, such as, 2,4,5,6-tetraminopyrimidine.

When 2-substituted 5-nitroso-4,6-diaminopyrimidine is obtained by the reaction of malonic dinitrile with an amidine in the presence of a nitrite salt in acid medium and in water or alcohol as a solvent to the amidine salt of isonitrosomalononitrile and by further conversion of this salt in dimethylformamide in a basic medium by heat treatment, a significant drawback of such process is the formation of dimethylnitrosoamine in small amounts (under certain circumstances) with the use of dimethylformamide as the solvent. The first embodiment of the invention is disclosed in European patent application No. 115,325, which was published after the filing date of U.S. Ser. No. 566,887 and Swiss patent application No. 482/83.

An object of the second embodiment of the invention is to avoid the drawbacks of the prior art and the first embodiment of and to provide a process that produces 2-substituted 5-nitroso-4,6-diaminopyrimidine in a simple, economical and particularly safe way and in high yield. The object is achieved by the process of the second embodiment of the invention.

The second embodiment of the invention involves a process for the production of 2-substituted 5-nitroso-4,6-diaminopyrimidines of the formula:

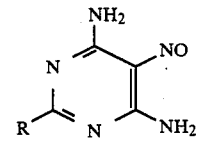

wherein R is aryl, alkyl, alkythio, amino, substituted amino or arylalkyl. Malonic dinitrile is reacted with an amidine of the formula:

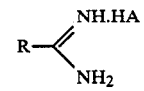

wherein A is Cl, $\frac{1}{2}SO_4$, $HSO_4$, $NO_3$, acetate or phosphate and R has the meaning given above, in water or alcohol in an acid medium in the presence of a nitrite salt to the corresponding amidine salt of the isonitrosomalononitrile. The amidine salt of the isonitrosomalononitrile in a polar aprotic solvent is further converted by heat treatment to the end product. Dimethyl sulfoxide, N-methyl-2-pyrrolidone, N,N-dimethylacetamide, hexamethyl-phosphoramide, 1,3-dimethyl-2-oxo-hexahydropyrimidine, tetrahydrothiophene 1,1-dioxide, 2-methylglutarodinitrile or cyclohexanone is used as the polar aprotic solvent for the reaction of the amidine salt of isonitrosomalononitrile for the corresponding 2-substituted 5-nitroso-4,6-diaminopyrimidine.

Preferably the 5-nitroso-2,4,6-triaminopyrimidine is produced by reaction of malonic dinitrile with guanidine hydrochloride in water at a pH below 6.9 in the presence of sodium nitrite to the guanidine salt of the isonitrosomalononitrile, wherein the further conversion of this salt to the end product takes place in dimethyl sulfoxide by means of heat treatment.

The invention reaction takes place according to general equation:

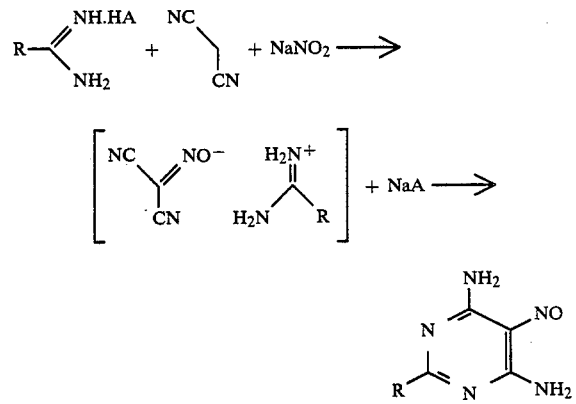

wherein A is Cl, $\frac{1}{2}SO_4$, $HSO_4$, $NO_3$ acetate or phosphate and R denotes aryl, alkyl, alkylthio, amino, substituted amino or arylalkyl.

Examples of amidines are acetamidine hydrochloride, benzamidine hydrochloride, S-methylisothiourea sulfate and guanidine hydrochloride. Preferably quanidine hydrochloride is used as the amidine. The alkali metal or alkaline earth metal nitrites, preferably sodium nitrite, can be used as the nitrite salt. Regarding the proportions, advantageously 0.1 to 1.1 mol of nitrite, preferably 1.0 mole to 1.02 mol of nitrite, is used per mol of malonic dinitrile. (This paragraph and the immediate above paragraph apply to both embodiments of the invention.)

Alkali or alkaline-earth metal nitrites, preferably sodium nitrite, can be used as the nitrite salt.

Herein an acid medium is understood to be a pH less than 6.9.

The amount of solvent for the first reaction stage is not critical and preferably is 200 to 2000 ml per mole of malonic dinitrile. Preferably 300 to 400 ml of solvent per mole of malonic dinitrile is used. The reaction temperature for the first stage is advantageously between 10° and 50° C. After a reaction time of about 0.5 to 15 hours and after usual working-up, e.g., by filtering and subsequent drying, the amidine salt of isonitrosomalononitrile can be obtained.

But the amidine salt of isonitrosomalononitrile can also be used directly without isolation by the addition of dimethyl sulfoxide as the solvent in the second stage. In the second reaction stage, with dimethyl sulfoxide as the solvent, 100 to 2000 ml, preferably 300 to 800 ml, of solvent can be used per mole of malonic dinitrile.

The necessary basic medium can advantageously be obtained by the addition of sodium hydroxide, sodium carbonate, potassium hydroxide, potassium carbonate or substituted pyridines.

Sodium carbonate and potassium carbonate are the preferred bases.

For the final heat treatment, the reaction mixture is advantageously heated to a temperature of 100° to 180° C., preferably 130° to 160° C., advantageously for 0.25 to 6 hours, preferably 1 to 4 hours.

In a preferred version of the second embodiment, 5-nitroso-2,4,6-triaminopyrimidine is produced by malonic dinitrile and guanidine hydrochloride being converted at a pH below 6.9 in the presence of sodium nitrite to the guanidine salt of isonitrosomalononitrile and the guanidine salt of isonitrosomalononitrile is converted to 5-nitroso-2,4,6-triaminopyrimidine by heating to 150° C. in dimethyl sulfoxide and in the presence of $Na_2CO_3$.

The 2-substituted 5-nitroso-4,6-diaminopyrimidines present after the completed reaction can be separated in the usual way by filtering or centrifuging, washed with water and dried. The 2-substituted 5-nitroso-2,4,6-diaminopyrimidines, especially 5-nitroso-2,4,6-triaminopyrimidine, are versatile intermediate products, e.g., for production of medicines such as triamterene or methothrexate, and for the production of dye components such as 2,4,5,6-tetraaminopyrimidine.

This invention also includes a composition of malonic dinitrile, water or alcohol, a nitrite salt and an amidine having the formula:

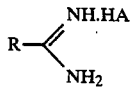

wherein A is Cl, $\frac{1}{2}SO_4$, $HSO_4$, $NO_3$, acetate or phosphate and R is aryl, alkyl, alkylthio, amino, substituted amino or arylalkyl. The pH is acidic.

DETAILED DESCRIPTION OF THE INVENTION

As used herein, all percentages, ratios, proportions and parts are on a weight basis unless otherwise stated herein or otherwise obvious herefrom to one skilled in the art.

EXAMPLE 1

A solution of 70 g of sodium nitrite in 120 ml of water was added drop by drop to a suspension of 66 g of malonic dinitrile and 100 g of guanidine hydrochloride in 200 g of water at pH 4 and room temperature. After 4 hours of stirring at room temperature, 21 g of sodium carbonate and 770 g of a polar aprotic solvent were added and the water distilled off at reduced pressure. Then the reaction mixture was heated for 3 hours at 140° to 150° C., during which isomerization to 5-nitroso-2,4,6-triaminopyrimidine took place. After the reaction was completed, 750 g of water was added and the product was filtered off and washed with water. The results of tests in various polar aprotic solvents are summarized in Table 1:

TABLE 1

| Example | Solvent | Product Amount, g | Yield, % |
|---------|---------|-------------------|----------|
| 1-1 | dimethyl sulfoxide | 138 | 89.6 |
| 1-2 | dimethylacetamide | 118 | 76.6 |
| 1-3 | N—methyl-2-pyrrolidone | 142 | 92.2 |
| 1-4 | tetrahydrothiophene 1,1-dioxide | 147 | 95.5 |
| 1-5 | 3-picoline | 130 | 84.4 |
| 1-6 | 4-picoline | 144 | 93.5 |
| 1-7 | 2-methyl-5-ethylpyridine | 151 | 98.0 |
| (1-8* | dimethylformamide | 128 | 83.1) |
| 1-9 | 2-methylglutarodinitrile | 111 | 72.1 |
| 1-10 | cyclohexanone | 86 | 55.8 |
| 1-11 | hexamethylphosphoramide | 141 | 91.6 |
| 1-12 | 1,3-dimethyl-2-oxo-hexahydropyrimidine | 145 | 94.2 |

Note:
*Comparison test

EXAMPLE 2

A solution of 37.5 g of sodium nitrite in 60 g of water was added drop by drop to a suspension of 33 g of malonic dinitrile and 52 g of acetamidine hydrochloride in 100 g of water at pH 4 and room temperature. After a 4-hour reaction, the reaction mixture was cooled to 0° C. and the product was filtered off. The acetamidine salt of isonitrosomalononitrile was obtained with a melting point of 142° to 143° C. (decomposition) in almost quantitative yield (84 percent isolated).

EXAMPLE 3

A solution of 14 g of sodium nitrite in 25 g of water was added drop by drop to a suspension of 13.2 g of malonic dinitrile and 32 g of benzamidine hydrochloride in 25 g of water at pH 3 to 5 and at 20° C. After a 5-hour reaction and cooling to 0° C., the reaction product was filtered by suction and was dried. The benzamidine salt of isonitrosomalononitrile was obtained with a melting point of 150° C. (decomposition) in almost quantitative yield (94 percent isolated).

EXAMPLE 4

A solution of 35 g of sodium nitrite in 60 ml of water was added drop by drop to a suspension of 33 g of malonic dinitrile and 70 g of S-methylisothiourea sulfate in 100 ml of water at pH 4 and room temperature. After a 5-hour reaction, the reaction mixture was cooled to 4° C. and was filtered off. After drying, the S-methylisothiouronium salt of isonitrosomalononitrile was obtained in very high yield (76 percent isolated) with a melting point of 123°–124° C. (decomposition).

EXAMPLE 5

A solution of 70 g of sodium nitrite in 120 ml of water was added drop by drop to a suspension of 66 g of malonic dinitrile and 97 g of guanidine hydrochloride in 120 ml of water at pH 4 and room temperature. After 4 hours stirring it was cooled to 0° C. and was filtered off. After drying in a vacuum the guanidine salt of isonitrosomalononitrile was obtained in almost quantitative yield (84 percent isolated), with a melting point of 160° to 161° C. (decomposition).

Further conversion of these amidine salts of isonitrosomalononitrile of Examples 2 to 5 to the corresponding 2-substituted 5-nitroso-4,6-diaminopyrimidines can be performed as described in the literature, E. C. Taylor et al., J. Am. Chem. Soc. 81, 2442 (1959).

EXAMPLE 6

A solution of 70 g of sodium nitrite in 120 g of water was added dropwise at room temperature to a suspension of 66 g of malononitrile and 96 g of guanidine hydrochloride in 200 g of water, and the pH was kept at 4 by the addition of hydrochloric acid. After the reaction had continued for 4 hours at room temperature, 21 g of sodium carbonate and 400 g of dimethylformamide were added. The water was distilled off under reduced pressure. Thereafter, the reaction mixture was heated at 140° C. for 1 hour, isomerization to 5-nitroso-2,4,6-triamino-pyrimidine taking place. After the reaction was complete, 400 ml of water were added, and the product was filtered off and washed with water. After the product had been dried, 140 g of a pure raspberry-red 5-nitroso-2,4,6-triaminopyrimidine were obtained. The melting point of the product was above 340° C. and the yield was 91 percent.

EXAMPLE 7

A solution of 37.5 g of sodium nitrite in 60 g of water was added dropwise to a suspension of 33 g of malononitrile and 52 g of acetamidine hydrochloride in 100 g of water at pH 4 and at room temperature. After the reaction had continued for 4 hours, the reaction mixture was cooled to 0° C. and the product was filtered off. The acetamidine salt of isonitrosomalononitrile, having a melting point 142° to 143° C. (decomposition), was obtained in virtually quantitative yield (84 percent isolated).

EXAMPLE 8

A solution of 14 g of sodium nitrite in 25 g of water was added dropwise to a suspension of 13.2 g of malononitrile and 32 g of benzamidine hydrochloride in 25 g of water at pH 3 to 5 and at 20° C. After the reaction had continued for 5 hours and the mixture had been cooled to 0° C., the reaction product was filtered off under suction and dried. The benzamidine salt of isonitrosomalononitrile, having a melting point of 150° C. (decomposition), was obtained in virtually quantitative yield (94 percent isolated).

EXAMPLE 9

A solution of 35 g of sodium nitrite in 60 ml of water was added dropwise to a suspension of 33 g of malononitrile and 70 g of S-methylisothiourea sulfate in 100 ml of water at pH 4 and at room temperature. After the reaction had continued for 5 hours, the reaction mixture was cooled to 4° C., and the product was filtered off. After the product had been dried, the S-methylisothiouronium salt of isonitrosomalononitrile was obtained in very high yield (76 percent isolated). The salt had a melting point of 123° to 124° C. (decomposition).

EXAMPLE 10

A solution of 70 g of sodium nitrite in 120 ml of water was added dropwise to a suspension of 66 g of malononitrile and 97 g of guanidine hydrochloride in 120 ml of water at pH 4 and at room temperature. The mixture was stirred for 4 hours and then was cooled to 0° C., and the product was filtered off. After the product had been dried under vacuum, the guanidine salt of isonitrosomalononitrile was obtained in virtually quantitative yield (84 percent isolated). The salt had a melting point of 160° to 161° C. (decomposition).

What is claimed is:

1. Process for the production of a 2-substituted-5-nitroso-4,6-diaminopyrimidine of the formula:

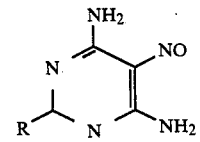

wherein R is aryl, alkyl, alkythio, amino, substituted amino or arylalkyl, comprising (a) reacting malonic dinitrile with an amidine of the formula:

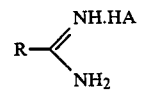

wherein A is Cl, ½SO4, HSO4, NO3, acetate or phosphate and R has the meaning given above, in water or alcohol, in an acid medium and in the presence of a nitrite salt, to give the corresponding amidine salt of isonitrosomalononitrile; and (b) converting the amidine salt of isonitrosomalononitrile in a polar aprotic solvent by heat treatment to the corresponding 2-substituted-5-nitroso-4,6-diaminopyrimidine, dimethyl sulfoxide, N-methyl-2-pyrrolidone, N,N-dimethylacetamide, hexamethyl-phosphoramide, 1,3-dimethyl-2-oxohexahydropyrimidine, tetrahydrothiophene 1,1-dioxide, 2-methylglutaro-dinitrile or cyclohexanone being used as the polar aprotic solvent for reaction of the amide salt of isonitrosomalononitrile to the corresponding 2-substituted 5-nitroso-4,6-diaminopyrimide.

2. Process as claimed in claim 1 wherein, for the production of the 5-nitroso-2,4,6-triaminopyrimidine, the amidine is guanidine hydrochloride, the nitrite salt is sodium nitrite, and the malonic dinitrile is reacted with the guanidine hydrochloride in the water at a pH below 6.9 in the presence of the sodium nitrite to the guanidine salt of the isonitrosomalononitrile, and converting said salt to the 2-substituted-5-nitroso-4,6-diaminopyrimide in dimethyl sulfoxide by heat treatment.

3. Process for the preparation of a 2-substituted 5-nitroso-4,6-diaminopyrimidine having the formula:

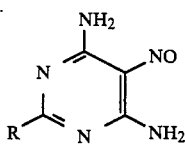

wherein R is aryl, alkyl, alkylthio, amino, substituted amino or arylalkyl, comprising: (a) reacting malonic dinitrile with an amidine having the formula:

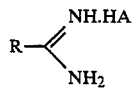

wherein A is Cl, ½SO$_4$, HSO$_4$, NO$_3$, acetate or phosphate and R has the meaning given above, in water or alcohol, in an acidic medium and in the presence of a nitrite salt, to give the corresponding amidine salt of isonitrosomalononitrile; and (b) converting the amidine salt of isonitrosomalononitrile, in dimethylformamide or a pyridine base, and in a basic medium, by heat treatment to the corresponding 2-substituted-5-nitroso-4,6-diaminopyrimidine.

4. Process as claimed in claim 3 wherein step (a) process is carried out in an acidic medium at a pH of below 6.9.

5. Process as claimed in claim 4 wherein an alkali metal nitrite or an alkaline earth metal nitrite, is used as the nitrite salt.

6. Process as claimed in claim 5 wherein the alkali metal nitrite is sodium nitrite.

7. Process as claimed in claim 7 wherein, for the preparation of 5-nitroso-2,4,6-triaminopyrimidine, the amidine is guanidine hydrochloride, the nitrite salt is sodium nitrite, and malonic dinitrile is reacted with guanidine hydrochloride in water at a pH of below 6.9, in the presence of sodium nitrite, to give the guanidine salt of isonitrosomalononitrile, and the guanidine salt of isonitrosomalononitrile, in a basic medium, is converted to 5-nitroso-2,4,6-triaminopyrimidine by boiling under reflux in a solvent.

8. Process as claimed in claim 5 wherein the water or alcohol is removed between step (a) and step (b).

9. Process as claimed in claim 8 wherein dimethylformamide is present in step (b).

10. Process as claimed in claim 8 wherein a pyridine base is present in step (b).

11. Process as claimed in claim 3 wherein the nitrite salt is an alkali metal nitrite or an alkaline earth metal nitrite.

* * * * *